United States Patent [19]

Nishikawa et al.

[11] Patent Number: 4,900,807

[45] Date of Patent: Feb. 13, 1990

[54] POLYMER FROM NITRILE TERMINATED COMPOUNDS HAVING SCHIFF BONDS AND PROCESS FOR PREPARING THE SAME

[75] Inventors: Akio Nishikawa; Toru Koyama, both of Hitachi; Hideki Asano, Mito; Toshikazu Narahara, Ibaraki, all of Japan

[73] Assignee: Hitachi, Ltd., Tokyo, Japan

[21] Appl. No.: 151,510

[22] Filed: Feb. 2, 1988

[30] Foreign Application Priority Data

Feb. 20, 1987 [JP] Japan .................................. 62-35562

[51] Int. Cl.⁴ ...................... C08G 83/00; C08G 73/00
[52] U.S. Cl. .................... 528/362; 528/206; 528/322; 558/303
[58] Field of Search ........................ 528/362, 206, 322

[56] References Cited

U.S. PATENT DOCUMENTS

| | | | |
|---|---|---|---|
| 3,933,630 | 11/1976 | Darmory et al. | 260/78 |
| 4,055,543 | 10/1977 | D'Alelio | 260/47 |
| 4,066,609 | 1/1978 | Darmory et al. | 260/42.13 |
| 4,102,873 | 7/1978 | Griffith et al. | 528/362 |
| 4,105,646 | 8/1978 | Winter | 528/311 |
| 4,178,430 | 12/1979 | Billow | 528/245 |
| 4,555,565 | 11/1985 | Hsu | 528/362 |

FOREIGN PATENT DOCUMENTS 809410 2/1959 United Kingdom.

OTHER PUBLICATIONS

Journal Chem. Soc., 1976, pp. 300–301.
Synthesis, No. 6, 6.81, pp. 442–444.
Chem. Abstracts, vol. 79, Nov. 1973, p. 326, 125445m.
Chem. Abstracts, vol. 95, Nov. 1981, p. 27, 170155R.

*Primary Examiner*—Harold D. Anderson
*Attorney, Agent, or Firm*—Fay, Sharpe, Beall, Fagan, Minnich & McKee

[57] ABSTRACT

There are disclosed a nitrile-terminated Schiff compound represented by the formula $X(Z-Y-C\equiv N)_m$ (I) wherein n is 1 or 2, Z is $-CH=N-$ or $-N=CH-$ and Y is a divalent organic group such as phenylene and the like, and X is the same as Y when n=2 or H, lower alkyl group etc. when n=1; polymers obtained by polymerizing said Schiff compound alone or together with other monomers, and a process for preparing such a polymer therefrom.

22 Claims, 1 Drawing Sheet

POLYMER FROM NITRILE TERMINATED COMPOUNDS HAVING SCHIFF BONDS AND PROCESS FOR PREPARING THE SAME

FIELD OF THE INVENTION

This invention relates to the nitrile-terminated Schiff compounds capable of forming polymers with excellent heat resistance on heating, the polymers obtained from such compounds, and a process for preparing such polymers.

RELATED ART

In the fields of electronic parts and electrical apparatus, there is seen a trend toward higher packaging density, higher reliability, smaller size and weight, and higher performance. For attaining them, need is rising for an organic material having high heat resistance and excellent moldability (viz. curable at low temperatures and having high fluidity) so that the material can be readily turned into a cured product with a small coefficient of thermal expansion. Hitherto, N-substituted maleimides have been developed as such material and their practical application has been studied.

The materials based on said compounds, however, have many problems to be solved such as high curing temperature (higher than 200°C.) of the materials, poor adhesiveness to nonmetallic inorganic materials and metals, limited scope of utilization for varnish, coating material, etc., due to poor solubility in solvents, and low heat resistance in comparison with condensed imide type materials, and thus the practical application of said materials has been subject to limitations. Recently, use of ethynyl-terminated imide type materials for laminating material, adhesives, etc., has been studied in earnest, but these materials also have the problem in their fluidity at the time of molding and curing.

U.S. Pat. No. 4,178,430 gives disclosures relating to ethynyl-terminated Schiff compounds. According to this patent, said compounds are aromatic compounds, and it is stated that these compounds, when heated, produce a polymer having acetylene-acetylene recurrence or ene-yne linkage in the chain, and that such polymer can be utilized as a conductor or semiconductor material. Such polymer, however, because of its structural characteristics such as mentioned above, involves problems in its application to the fields where the electrical insulating properties are required, such as the field of electronic parts and electrical apparatus.

Thus, said conventional materials had difficulties in acquiring a balance of the properties such as heat resistance, moldability, electrical insulating properties, etc., required in application to the fields of electronic parts and electrical apparatus.

Especially, in the case of N-substituted maleimide materials which have been predominantly used as addition type reaction material, when it is attempted to take a balance among said properties, said materials are bound to be deteriorated in heat resistance, making it difficult to attain the intended object, i.e., realization of high performance, high reliability, etc., of the products using said materials.

OBJECT AND SUMMARY OF THE INVENTION

The object of this invention is to provide novel addition reaction compounds, polymers of said compounds, and a process for preparing such polymers, whereby said problems of the prior art can be solved.

The monomers provided in accordance with this invention are Schiff compounds having Schiff bonds in the molecular chain and a nitrile group at the terminal and represented by the following general formula (I):

$$X\text{---}(Z\text{---}Y\text{---}C\equiv N)_n \quad (I)$$

wherein n is a number of 1 or 2; z represents $-CH=N-$ or $-N=CH-$, and when $n=2$ both Z's are the same and represent either $-CH=N-$ or $-N=CH-$; when $n=1$, X represents H, a $C_1$-$C_8$ alkyl group, an aryl group which may be substituted, such as phenyl, naphthyl, etc., or a $C_3$-$C_6$ cycloalkyl group, and when $n=2$, X represents a divalent organic group such as alkylene, arylene, etc.; Y represents a divalent organic group which may be the same as or different from X; when $n=2$, all of X, Y and Z may be the same or different from each other, or two of them may be the same and different from the remaining one.

The polymers provided according to this invention are the ones obtainable by polymerizing the compounds of formula (I) as monomers, and especially those polymers which have a novel skeleton in their structure.

The process for preparing the polymers according to this invention is a process for preparing the polymers having a novel skeleton in their structure as mentioned above.

DETAILED DESCRIPTION OF PREFERRED EMBODIMENTS

Figure 1:
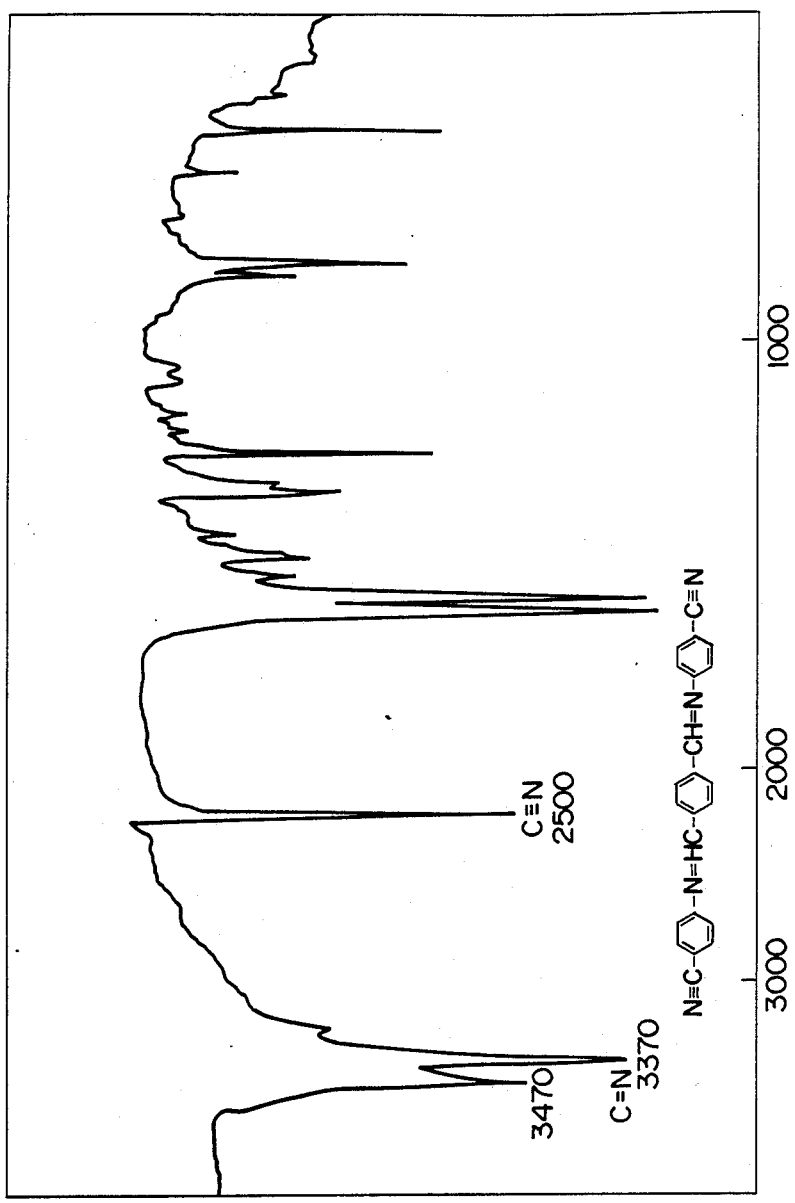
FIGURE 1 shows an infrared absorption spectrum of a nitrile-terminated Schiff compound according to this invention.

One aspect of the present invention is directed to nitrile-terminated Schiff compounds represented by the general formula (I):

$$X\text{---}(Z\text{---}Y\text{---}C\equiv N)_n \quad (I)$$

In the above formula (I), n is a number of 1 or 2, and Z represents $-CH=N-$ or $-N=CH-$. Even when $n=2$, Z's represent the same, either $-CH=N-$ or $-N=CH-$.

When $n=1$, X represents H, a $C_1$-$C_8$ alkyl group, a phenyl group which may have a substituent (preferred examples of such substituent being F, Cl, Br, $CH_3$, $CF_3$, OH, $NH_2$,

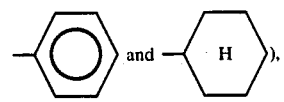

a naphthyl group which may have a substituent (preferred examples of such substituent being the same as mentioned above), or a $C_3$-$C_6$ cycloalkyl group, and Y represents a divalent organic group, preferably a $C_1$-$C_{12}$ alkylene group which may have a branch, an arylene group which may be substituted (preferred examples of substituent being those mentioned above), such as phenylene, naphthylene, biphenylene, anthracene, phenanthrene, pyrene or like group which may have a substituent,

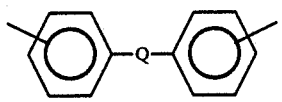

{wherein Q represents O, S, SO$_2$, -(CH$_2$)$_{\overline{m}}$ (m representing a number of 1 to 12),

-(CF$_2$)$_{\overline{m}}$ (m being as defined above,

(wherein R$^1$ and R$^2$ may be the same or different and represent H, CH$_3$, C$_2$H$_5$, CF$_3$,

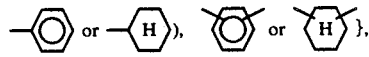

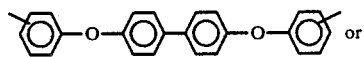

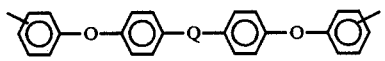

(Q representing the same as defined above).

When n=2, X represents a divalent organic group like Y, examples thereof including those mentioned above. X and Y may be the same or different from each other. Two Y's may be the same or different from each other Another aspect of the present invention is directed to the polymers having a so-called cross-ladder skeleton centered by a dihydrotriazine ring which are obtainable by polymerizing the nitrile-terminated Schiff compounds of said formula (I) used as a part or whole of the monomer. The term "cross-ladder skeleton", which will be described in detail later, is used in this specification to refer to a skeleton comprising recurrence of the following structural units centered by a 1,2-dihydro-1,3,5-triazine ring:

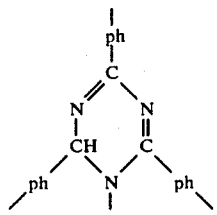

(wherein ph represents an aromatic residue such as phenylene group).

In still another aspect of this invention, it provides a process for preparing polymers having a cross-ladder skeleton comprising polymerization of said compounds of formula (I).

The compounds of formula (I) provided in accordance with this invention can be subclassed into the following four groups:

Compounds of the formula:

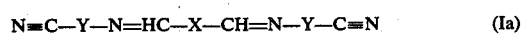

(viz. The compounds of formula (I) where n=2 and Z=—CH=N—)

Compounds of the formula:

(viz. the compounds of formula (I) where n=2 and Z=—N=CH—)

Compounds of the formula:

(viz. the compounds of formula (I) where n=1 and Z=—CH=N—)

Compounds of the formula:

(viz. the compounds of formula (I) where n=1 and Z=—N=CH—)

In the above formulae (Ia–Id), X and Y are as defined above).

In the present invention, the nitrile-terminated compounds having at least two Schiff bonds, which are represented by the formula (Ia):

(wherein X and Y are as defined above) can be synthesized very easily by a reaction represented by the following formula:

OCH—X—CHO + H$_2$N—Y—C≡N +

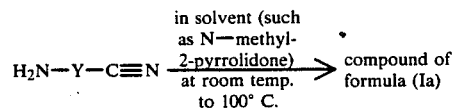

(In the above formula, X and Y are as defined above, and Y's may be the same or different from each other).

In the above formula (Ia), regarding X and Y therein, it is especially preferred when X is —(CH$_2$)$_{\overline{m'}}$ (m' being a number of 1 to 8),

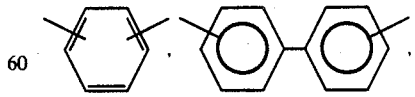

{Q representing

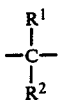

(wherein R¹ and R² represent H, CH₃, C₂H₅, CF₃,

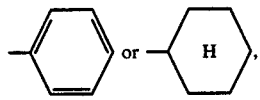

and they may be the same or different from each other), O, CO, S or SO₂},

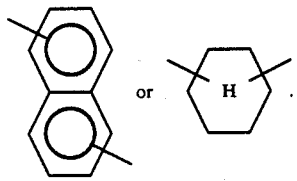

In the present invention, the nitrile-terminated compounds having at least two Schiff bonds, represented by the formula Ib):

$$N\equiv C-Y-CH=N-X-N=CH-Y-C\equiv N \quad (Ib)$$

(wherein X and Y are as defined above) can be synthesized by a reaction represented by the following formula:

$$OHC-Y-C\equiv N + OHC-Y-C\equiv N +$$

$$H_2N-X-NH_2 \xrightarrow[\text{at room temp.}]{\text{in solvent (such as N—methyl-2-pyrrolidone)}} \text{compound of formula (Ib)}$$

(In the above formula, Y and X are as defined above, and Y's may be the same or different from each other).

Among the compounds of formula (Ib), especially preferred are those of the formula in which X is $-(CH_2)_m-$ (m being as defined above),

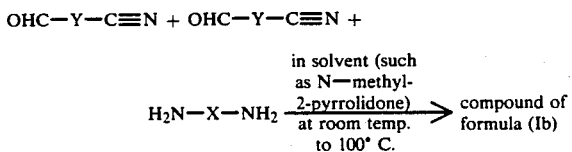

{Q representing

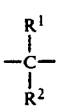

(wherein R¹ and R² may be the same or different from each other and represent H, CH₃, C₂H₅, CF₃,

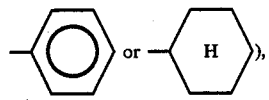

O, CO, S, SO₂ or

},

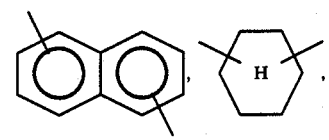

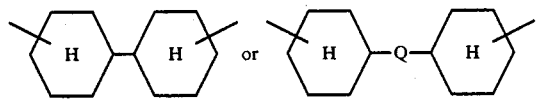

(Q representing the same as defined above).

Also, in the present invention, the nitrile-terminated Schiff compounds represented by the formulae (Ic) and/or (Id):

$$X-CH=N-Y-C\equiv N \quad (Ic)$$

$$X-N=CH-Y-C\equiv N \quad (Id)$$

(wherein X and Y are as defined above) can be synthesized by, for instance, reacting monofunctional aldehyde compounds and aminonitrile compounds in a suitable solvent (such as N-methyl-2-pyrrolidone) at a temperature in the range from room temperature to 100° C. as shown by the following reaction formulae 1-6:

1.
 →

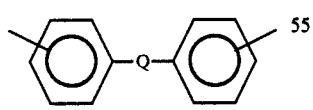

2.
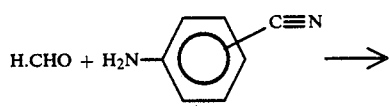 →

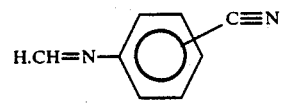

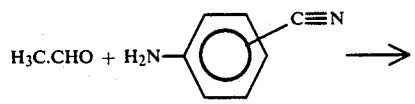

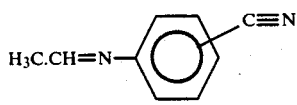

-continued

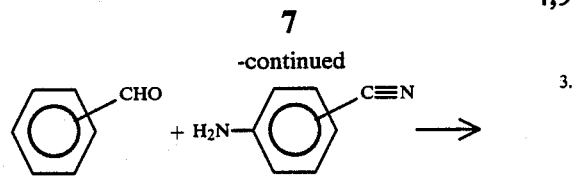
3.

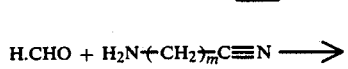
4.

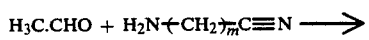
5.

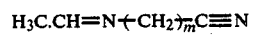

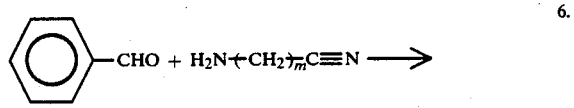
6.

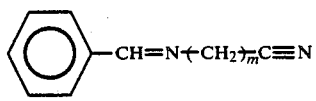

(wherein m is a number of 1 to 12).

Among the compounds represented by the formulae (Ic) and (Id), those of the formulae in which X is H, a $C_1$-$C_8$ alkyl group,

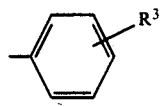

($R^3$ representing H, F, Cl, Br, $CH_3$, $CF_3$, OH, $NH_2$,

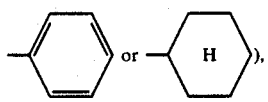

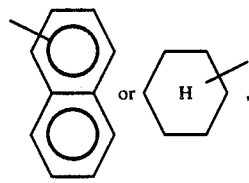

and Y is $+CH_2)_m$ (m being as defined above),

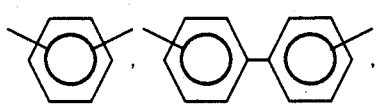

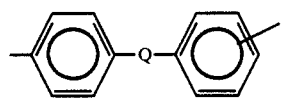

{Q representing —$CH_2)_m$ (m being as defined as above), —O—, —CH—, —S—, —$SO_2$—, $$-\underset{R^2}{\underset{|}{\overset{R^1}{\overset{|}{C}}}}-$$

($R^1$ and $R^2$ being as defined above) or

are especially preferred.

As the aldehyde compound used as an essential component in the synthesis of the compounds of formula (I) according to this invention, the following can be mentioned as examples: aliphatic saturated aldehydes such as formaldehyde, acetaldehyde, propionaldehyde, butylaldehyde, isobutylaldehyde, valeraldehyde, isovaleraldehyde, hydrinealdehyde, caproic aldehyde, heptaldehyde, caprylaldehyde, pelargonaldehyde, capric aldehyde, undecylaldehyde, lauric aldehyde, dodecylaldehyde and stearic aldehyde; aliphatic dialdehydes such as glyoxal and succinic dialdehyde; keto-aldehydes such as methylglyoxal, acetoacetaldehyde, levulinic aldehyde and phenylglyoxal; aliphatic unsaturated aldehydes such as acroleincrotonaldehyde and propiolaldehyde; aromatic aldehydes such as benzaldehyde, o-tolualdehyde, m-tolualdehyde, p-tolualdehyde, salicylaldehyde, cinnamaldehyde, α-naphthaldehyde, β-naphthaldehyde, isophthaldehyde, terephthaldehyde and phthaldehydric acid; nitrogen-containing cyclic aldehydes such as piperidine-2-aldehyde, pyridine-2-aldehyde, pyridine-3-aldehyde, pyridine-4-aldehyde, pyridine-2,6-dialdehyde, pyridine-2,4-dialdehyde and pyridine-3,5- dialdehyde; and other known heterocyclic aldehydes such as furfural.

The aminonitrile compounds represented by the formula $H_2N$—Y—C≡N, used as another essential component in the synthesis of the compounds of formula (I) according to this invention, include, for example, 3-aminobenzonitrile, 4-aminobenzonitrile, 3-amino-3'-nitrilbiphenyl, 4-amino-4'-nitrilediphenylmethane, 4-amino-4'-nitrilediphenylether, 3-aminophthalonitrile and 4-aminophthalonitrile.

The aldehydonitrile compounds represented by the formula OHC—Y—C≡N include, for example 3-aldehydrobenzonitrile, 4-aldehydobenzonitrile, 3-aldehydo-3'-nitrilebiphenyl, 4-aldehydo-4'-nitrilediphenylmethane, and 4-aldehydo-4'-nitrilediphenylether.

In preparation of polymers according to this invention, an ethylenic polymerizable compound may be added to the compounds of this invention as a crosslinking agent in an amount not impairing the effect of the invention, for example, 1 to 900 parts by weight to 100 parts by weight of the Schiff compound of this invention, Examples of such additive compound are styrene, vinyltoluene, α-methylstyrene, divinylbenzene, diallyl phthalate, diallyl phthalate polymers, chlorostyrene, dichlorostyrene, bromostyrene, dibromostyrene, diallylbenzene sulfonate, diallylaryl phosphonate, diallylarylphosphinic acid esters, acrylic esters, methacrylic esters, triallyl cyanurate, triallyl cyanurate prepolymers, tribromophenolallylether and unsaturated polyester resins. These compounds may be used in combination.

The Schiff compounds of this invention may be also mixed with one or more of the N,N'-substituted bismaleimide compounds represented by the following formula:

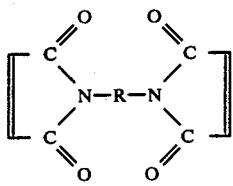

(wherein R represents an alkylene group, an allylene group or a substituted divalent organic group thereof), the examples of such compounds being N,N'-ethylenebismaleimide, N,N'-hexamethylenebismaleimide, N,N'-dodecamethylenebismaleimide, N,N'-m-phenylenebismaleimide, N,N'-4,4'-diphenyletherbismaleimide, N,N'-4,4'-diphenylmethanebismaleimide, N,N'-4,4'-dicyclohexylmethanebismaleimide, N,N'-4,4'-methaxylenebismaleimide and N,N'-4,4'-diphenylcyclohexanebismaleimide. Also, mixtures of mono-substituted maleimides, tri-substituted maleimides or tetra-substituted maleimides and said substituted bismaleimides may be suitably selected and used according to the purpose of use and the desired properties of the produced polymer.

The compounds of this invention and the compositions containing such compounds can be applied to molding materials, laminating materials, coating materials, covering materials, adhesives, varnishes for various uses, ink material, toner material, liquid crystal material, conductors, nuclear reactor material, FRP material, pastes and the like. They find particularly useful applications to prepreg resins, interlaminar insulating films used in multi-layer lamination of LSI, protective coatings for LSI element surfaces, liquid crystal orienting films, adhesives for aerospace devices, molding materials, laminating materials, silver pastes and the like.

In practical application of the compounds of this invention to said uses, it is possible to use various types of solvent, for example, organic polar solvents such as N-methyl-2-pyrrolidone, N,N-dimethylacetamide, N,N-dimethylformamide, N,N-diethylformamide, N-methylformamide, dimethyl sulfoxide, N,N-diethylacetamide, hexamethylsulforamide, pyridine, dimethylsulfone, tetramethylsulfone, dimethyltetramethylenesulfone, etc., and phenolic solvents such as phenol, cresol, xylenol, etc. These solvents may be used singly or in combination. Non-solvents such as toluene, xylene, petroleum naphtha, etc., can be also used in limited amounts.

The compounds of this invention can be converted into a cured product with excellent high-temperature strength by short-time heating at a relatively low temperature. Also, they have excellent storage stability at or around room temperature and are capable of low-pressure molding owing to high fluidity at the time of molding, so that in their application to semiconductor sealants, laminating material or such, they guarantee an increased degree of freedom of molding workability.

Further, the compositions using the compounds of this invention can be mixed with one or more of the following materials according to the purpose of use.

For example, in case said compositions are used as molding material, it is possible to mix in said compositions various types of inorganic filler such as zircon, silica, molten quartz glass, clay, hydrated alumina, calcium carbonate, quartz glass, glass, asbestos, whisker, gypsum, magnesite, mica, kaolin, talc, graphite, cement, carbonyl iron, barium compounds, ferrite, lead compounds, molybdenum bisulfide, zinc white, titanium white, carbon black, silica sand, wollastonite, etc., various types of releasing agent such as fatty acids, waxes, etc., various types of coupling agent such as epoxysilane, vinylsilane, boran compounds, alkoxy-titanate compounds, and various types of metal chelate compounds. If necessary, various known types of flame retardants or additives composed of antimony, phosphorus, etc., can be used in combination with said materials.

The nitrile-terminated Schiff compounds of formula (I) can be polymerized by applying thereto an external energy such as heat or light to form a polymer having excellent heat resistance and a small coefficient of thermal expansion.

In case of polymerizing the compounds of this invention by heating, the polymerization needs to be carried out at a temperature preferably below the heat generation temperature at the time of polymerization, most preferably below 180° C. In the present invention, it is supposed from the infrared absorption spectra and X-ray diffraction analyses that the polymers obtained from the reactions under said conditions have a dihydrotriazine ring formed in their structural units.

This reaction procedure is illustrated more particularly by reaction formulae below:

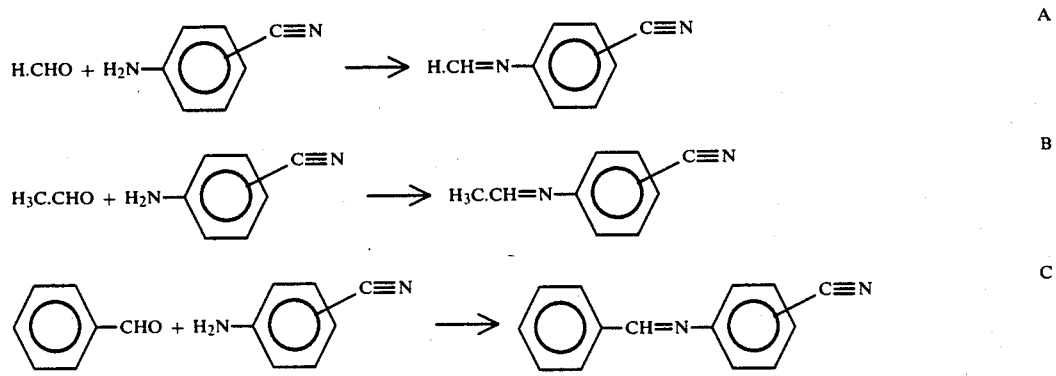

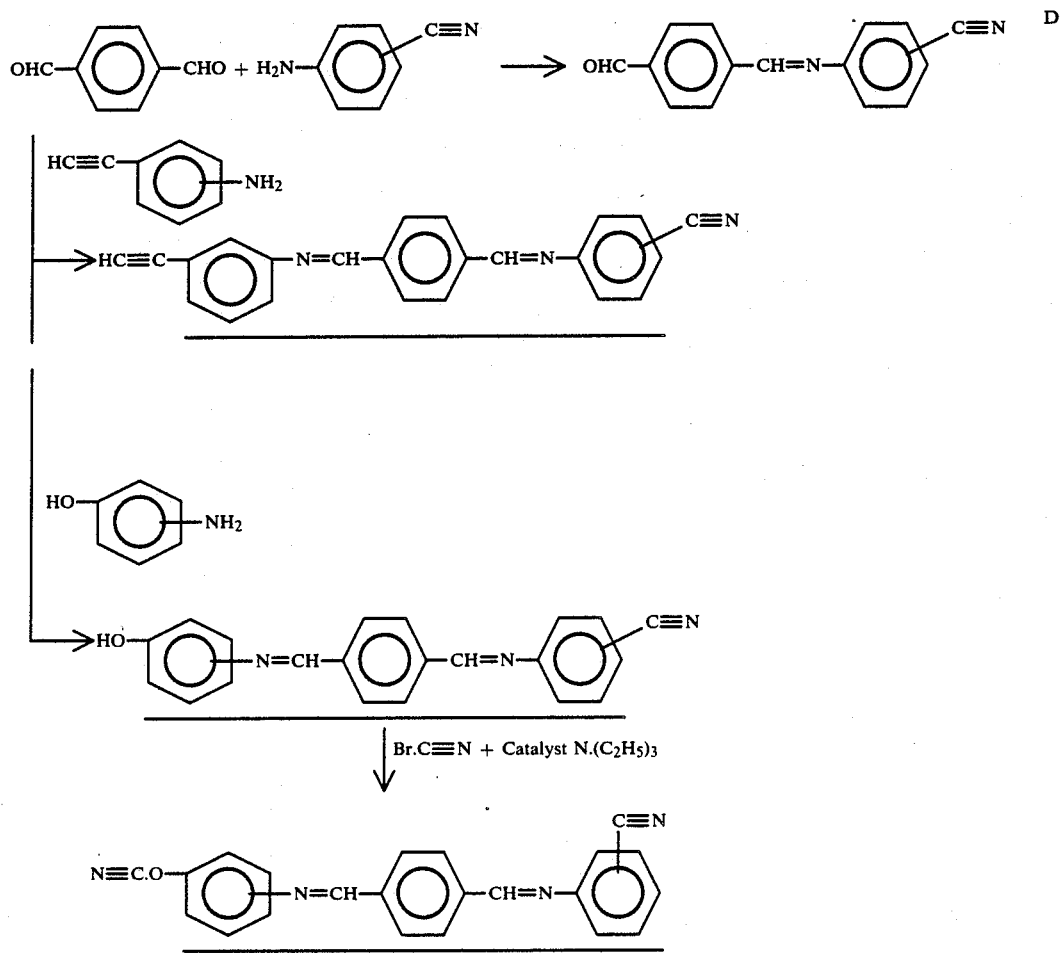
reaction product from formula C
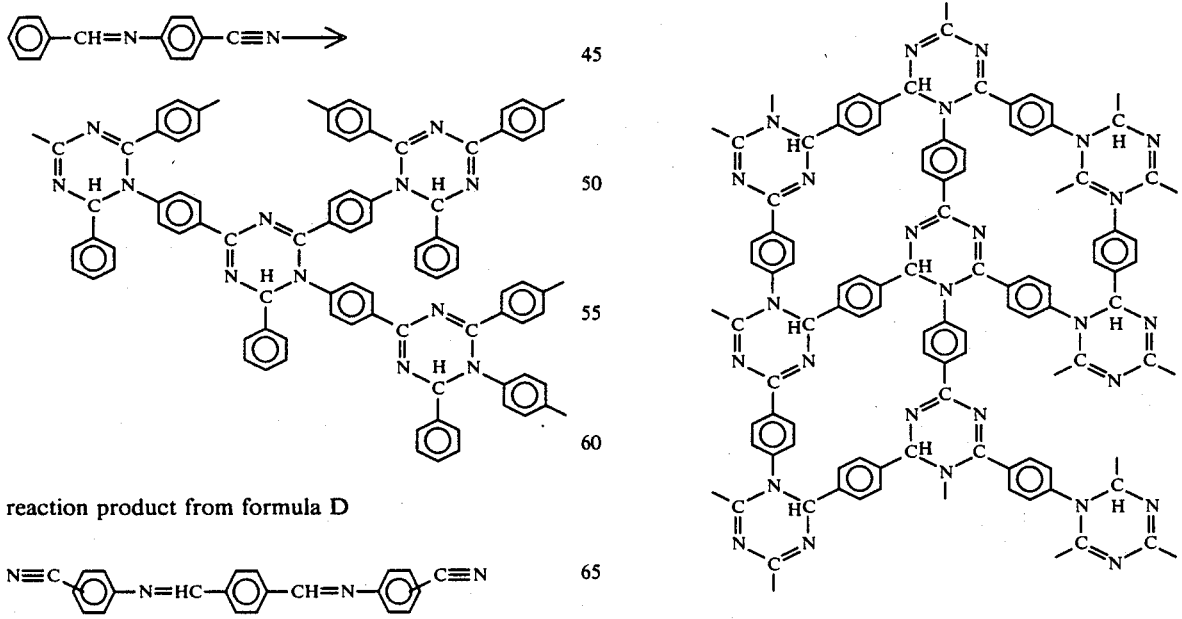
reaction product from formula D

EXAMPLES

Example 1

300 ml of N-methyl-2-pyrrolidone, 11.7 g (0.10 mol) of 3-aminobenzonitrile and 5.5 g (0.10 mol) of nitrileaminomethane were supplied into a 100 ml three-necked round flask provided with a stirrer. This was followed by the dropwise addition of a solution of 13.4 g (0.1 mol) of terephthalaldehyde in 200 ml of N-methyl-2-pyrrolidone under stirring at room temperature. The resulting mixture was stirred at room temperature for about 4 hours and further reacted in a heated state of 90°–120° C. for 5 hours. The reaction solution was poured into 3,000 ml of water, causing formation of a precipitate. After allowing the solution to stand for a whole day and night, the precipitate was filtered out, washed and then dried at 90°–100° C. for about 3 hours to obtain a reaction product having the following structural formula:

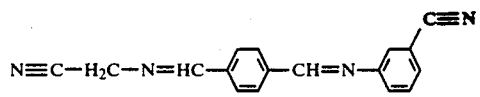
[A]

The melting point of said compound (A) was 107° C. and the peak heat generation temperature was 198° C.

Example 2

300 ml of N-methyl-2-pyrrolidone and 23.4 g (0.20 mol) of 4-aminobenzonitrile were supplied into a 1,000 ml three-necked round flask equipped with a stirrer, followed by the dropwise addition of a solution of 13.4 g (0.1 mol) of terephthalaldehyde in 200 ml of N-methyl-2-pyrrolidone under stirring at room temperature. The resulting mixture was stirred at room temperature for about 4 hours and then further stirred at 90°–100° C. for 5 hours. The reaction solution was poured into 3,000 ml of water, causing formation of a precipitate. After allowing the solution to stand for a whole day and night, the precipitate was filtered out, washed with pure water and then dried at 100°–110° C. for about 3 hours to obtain a reaction product having the following structural formula:

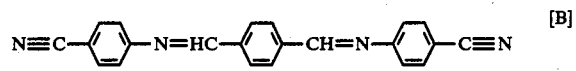
[B]

The melting point of this compound (B) was 135° C. and the peak heat generation temperature was 200° C. The infrared absorption spectrum of this compound is shown in FIG. 1.

The weight reduction starting temperature, 5% by weight reduction temperature (temperature at which 5% by weight reduction occurred) and coefficient of thermal expansion of the cured products of the nitrile-terminated Schiff compounds (A) and (B) obtained in Examples 1 and 2 and of an N-substituted maleimide type material BMI and an ethynyl-terminated imide type oligomer MC-600 (obtained according to U.S. Pat. No. 4,178,430) having the following structural formula, presented here by way of comparison, were measured and shown in Table 1.

TABLE 1

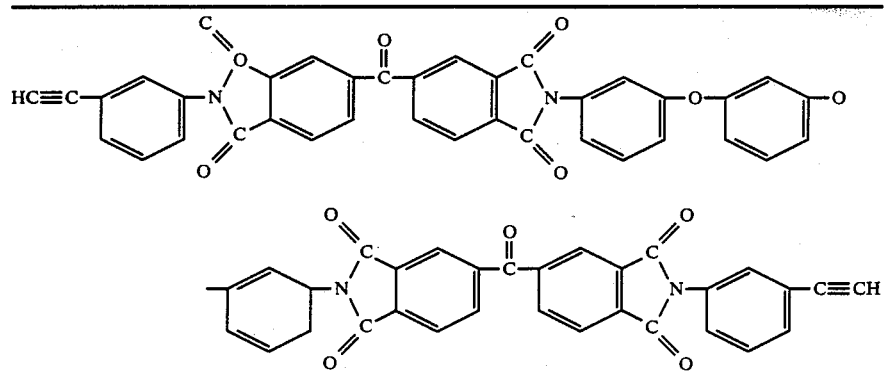

| Material | Melting point (°C.) | Peak heat generation temperature (°C.) | Weight reduction starting temperature (°C.) | 5% by weight reduction temperature (°C.) | Coefficient of thermal expansion ($\alpha \times 10^{-3}$) | Solubility in varnish-forming ketones |
|---|---|---|---|---|---|---|
| (A) | 107 | 198 | 390 | 510 | 0.8 | O |
| (B) | 135 | 200 | 426 | 549 | 0.8 | O |
| BMI | 155 | 200 | 369 | 473 | 1.5 | X |
| MC-600 | — | — | 358 | 506 | 1.4 | X |

EXAMPLE 3

The process of Example 2 was repeated but by using 11.0 g (0.20 mol) of nitrileaminomethane instead of 23.4 g of 4-aminobenzonitrile to obtain a reaction product of the following structural formula:

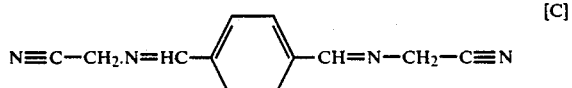
[C]

EXAMPLE 4

300 ml of N-methyl-2-pyrrolidone and 26.2 g (0.20 mol) of 4-aldehydobenzonitrile were supplied into a 1,000 ml three-necked round flask provided with a stirrer, followed by the dropwise addition of a solution of 10.8 g (0.10 mol) of paraphenylenediamine in 200 ml of N-methyl-2-pyrrolidone under stirring at room temperature. The mixture was stirred at room temperature for about 4 hours and then further stirred at 90°-100° C. for 2 hours. The reaction solution was poured into 3,000 ml of water, causing formation of a precipitate. The precipitate was filtered out, washed and dried to obtain a reaction product having the following structure:

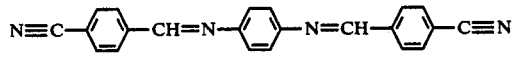
[D]

EXAMPLE 5

The process of Example 2 was followed except that 21.2 g (0.20 mol) of benzaldehyde was used instead of 13.4 g (0.10 mol) of terephthalaldehyde to obtain a reaction product of the following structural formula:

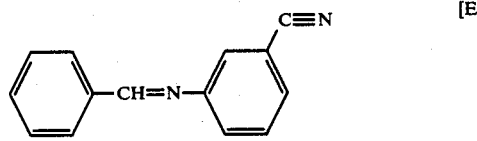
[E]

EXAMPLE 6

Example 4 was repeated by using 21.4 g (0.02 mol) of aniline instead of 10.8 g (0.10 mol) of paraphenylenediamine to obtain a reaction product of the following structure:

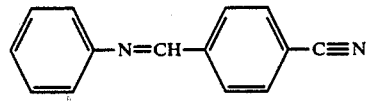
[F]

EXAMPLES 7-12 AND COMPARATIVE EXAMPLE

The reaction product of Example 1 having the structure:

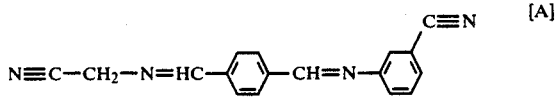
[A]

and the reaction product of Example 2 having the structure:

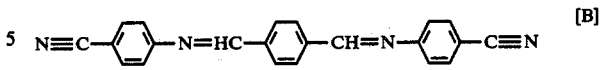
[B]

were chosen as examples of the nitrile-terminated Schiff compounds of this invention. With these compounds were blended severally an orthocresol novolak type polyglycidyl ether (epoxy equivalent: 195), 2,2-bis(4-(4-maleimidophenoxy)phenyl)propane, a novolak type phenolic resin and poly-p-hydroxystyrene in the prescribed amounts (parts by weight) shown in Table 2 to prepare 7 types of blends. To each of these blends were added 0.3 parts by weight of triphenylphosphine as cure promotor, 0.2 parts by weight of an epoxysilane KBM 403 (available from Shin'etsu Chemical Co., Ltd.) as coupling agent, 0.3 parts by weight of carnauba wax as releasing agent, 80% by weight of spherical silica powder having an average diameter of 5-10 μm as filler and 0.3 parts by weight of carbon black as colorant to form blend compositions as shown in Table 2. These blend compositions were kneaded under heating at 80°-90° C. for 10 minutes, then cooled and pulverized to obtain the molding materials for semiconductor sealing.

By using these molding materials for semiconductor sealing, 1M bit D-RAMLSI's were transfer molded under the conditions of 180° C., 70 kgf/cm$^2$ and 3 minutes to obtain the resin sealed semiconductor devices.

The results of reliability evaluations of said resin sealed semiconductor devices are shown in Table 2.

Moistureproofness reliability evaluation:

Each of said resin sealed semiconductor devices was left in a 121° C., 2 atm. supersaturated steam autoclave for a prescribed period of time (PCT), then taken out and checked for any abnormality in electrical operations. Those of the LSI's in which abnormality was detected and the cause of abnormality was corrosion break of wiring on the element were counted as defectives.

Cooling-heating cycle test evaluation:

Each of the resin sealed semiconductor devices was subjected to repeated cooling-heating cycles, each cycle comprising leaving the device in liquid nitrogen of −196° C. for 3 minutes and then immersing it in a silicone oil bath of +200 C. for 3 minutes, and thereafter checked for cracks and abnormality in electrical operations.

TABLE 2

| Composition and properties | Example 7 | 8 | 9 | 10 | 11 | 12 | Comp. Example |
|---|---|---|---|---|---|---|---|
| Composition (parts by weight) | | | | | | | |
| Nitrile-terminated Schiff compound (A) | 5.0 | — | — | — | — | — | — |
| Nitrile-terminated Schiff compound (B) | — | 5.0 | 5.0 | 5.0 | 10.0 | 10.0 | — |
| Orthocresol epoxy-novolak | 10.0 | 10.0 | 10.0 | 10.0 | — | — | 10.0 |
| 2,2-bis(4-(4-maleimidophenoxy)-phenyl)propane | 5.0 | 5.0 | — | — | 5.0 | — | — |
| Phenolic novolak resin HP-607N | — | — | 5.5 | — | — | — | 5.5 |
| Poly-p-hydroxystyrene | — | — | — | 6.0 | — | 5.0 | — |
| Moistureproofness reliability (percent defectives due to corrosion break of wiring) | | | | | | | |
| Time for which device was left in autoclave (hr) | | | | | | | |
| 500 | 0 | 0 | 0 | 0 | 0 | 0 | 0 |
| 1000 | 0 | 0 | 0 | 0 | 0 | 0 | 2 |
| 1500 | 0 | 0 | 0 | 0 | 0 | 0 | 18 |
| 2000 | 0 | 0 | 0 | 0 | 4 | 0 | 40 |
| 2500 | 2 | 0 | 0 | 6 | 22 | 8 | 98 |
| 3000 | 18 | 6 | 2 | 30 | — | 34 | — |
| Cooling-heating cycle durability (percent defectives | | | | | | | |

TABLE 2-continued

| Composition and properties | Example | | | | | | Comp. Example |
|---|---|---|---|---|---|---|---|
| | 7 | 8 | 9 | 10 | 11 | 12 | |
| due to cracking and abnormality in electrical operations) | | | | | | | |
| 50 | 0 | 0 | 0 | 0 | 0 | 0 | 4 |
| 100 | 0 | 0 | 0 | 0 | 0 | 0 | 52 |
| 150 | 0 | 0 | 0 | 0 | 0 | 0 | 100 |
| 200 | 8 | 0 | 0 | 0 | 0 | 0 | — |
| 400 | 18 | 0 | 0 | 0 | 6 | 2 | — |

EXAMPLES 13-19

Three compounds having the following structures:

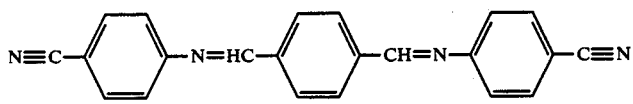

(B)

(G)

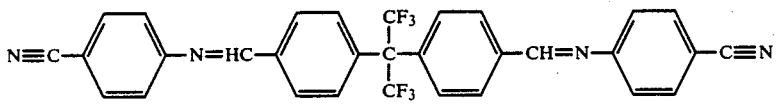

(H)

were taken up as examples of the nitrile-terminated Schiff compounds of this invention. These compounds were blended with 2,2-di-(4,4'-cyanatophenyl) propane, orthodiallylbisphenol F, 2,2-bis(4-(4-maleimidophenoxy)phenyl)hexafluoropropane and 4,4'-diphenylmethanebismaleimide in the prescribed amounts (parts by weight) shown in Table 3. The thus prepared blend compositions were dissolved in a mixed solution of equal amounts of N-methyl-2-pyrrolidone and methyl ethyl ketone to obtain varnishes containing 45-48% by weight of solids. These varnish solutions were then impregnated in a glass cloth (WE-116P-104, BY-54 available from Nitto Boseki Co., Ltd.) and dried at 160° C. for 20 minutes to obtain coated cloths with resin content of 45-48% by weight.

There were prepared 8 pieces of each coated cloth, and they were placed one on another with a 35 μthick TAI treated copper foil (available from Furukawa Denko CFC Co., Ltd.) placed on top bottom of the pile, and laminated under the conditions of 170°-180° C. and 40 kg f/cm² for 80 minutes to prepare, in all, double-side copper-clad laminates having a thickness of about 1.6 mm.

These copper-clad laminates were further cured at 200° C. for 240 minutes. The properties of the thus obtained copper-clad laminates are shown in Table 3.

Determination of properties:
A 25 mm × 100 mm test piece was cut out from each said copper-clad laminate, and the copper foil was etched away so that only a 10 mm wide copper foil would be left at the center of the test piece. Then the copper foil at the center of the test piece was peeled off in the vertical direction at a speed of 5 mm/min, and its peel strength was measured.

Soldering heat resistance
The 25 mm square test pieces cut out from the respective copper-clad laminates were placed floating in a 300° C. solder bath, and the time in which an abnormality such as blistering occurred on the test piece after placed in said solder bath was measured.

Flame extinguishing characteristics
Measured according to the UL-94 vertical method. The 12 mm wide and 125 mm long pieces were cut out from each copper-clad laminate, and these pieces were stripped of their copper foil by etching and used as test pieces. The test was conducted on 10 pieces from each laminate, and the flame extinguishing characteristics were shown by average flame-out time and scatter of flame-out time.

TABLE 3

| Composition and properties | Examples | | | | | | |
|---|---|---|---|---|---|---|---|
| | 13 | 14 | 15 | 16 | 17 | 18 | 19 |
| Composition (parts by weight) | | | | | | | |
| Nitrile-terminated Schiff compound (B) | 10.0 | 10.0 | 10.0 | 10.0 | 5.0 | — | — |
| Nitrile-terminated Schiff compound (G) | — | — | — | — | — | 10.0 | — |
| Nitrile-terminated Schiff compound (H) | — | — | — | — | — | — | 10.0 |
| 2,2-di-(4,4'-cyanatophenyl)propane | 10.0 | 5.0 | — | — | 5.0 | — | — |
| Orthodiallylbisphenol F | — | 5.0 | — | — | — | 5.0 | 5.0 |
| 2,2-bis-(4-(4-maleimidophenoxy)-phenyl)hexafluoropropane | — | — | 10.0 | 5.0 | 5.0 | 5.0 | 5.0 |
| 4,4'-diphenylmethanebismaleimide | — | — | — | 5.0 | 5.0 | — | — |
| Dicyanediamide | 0.5 | 0.5 | 0.5 | 0.5 | 0.5 | 0.5 | 0.5 |
| Benzoquanamine | — | — | — | 0.5 | 0.5 | 0.5 | 0.5 |
| Dicumyl peroxide | 0.3 | 0.3 | 0.3 | 0.3 | 0.3 | 0.3 | 0.3 |
| Coupling agent, epoxysilane KBM 403 | 0.2 | 0.2 | 0.2 | 0.2 | 0.2 | 0.2 | 0.2 |

| Composition and properties | Examples | | | | | | |
|---|---|---|---|---|---|---|---|
| | 13 | 14 | 15 | 16 | 17 | 18 | 19 |
| Properties | | | | | | | |
| Copper foil peel strength (kg/cm) | 1.9 | 1.9 | 2.1 | 1.9 | 2.0 | 1.9 | 2.3 |
| Solder heat resistance at 300° C. (sec) | >180 | >180 | >180 | >180 | >180 | >180 | >180 |
| Glass transition temperature (°C.) | | | | | | | |
| Flame extinguishing characteristics | 5 | 5 | 4 | 5 | 5 | 6 | 6 |
| | 0–10 | 0–7 | 0–7 | 0–8 | 0–8 | 0–10 | 0–11 |
| Dielectric constant (ε) | 3.7 | 3.6 | 3.2 | 3.3 | 3.4 | 3.3 | 3.3 |

According to the present invention, as described above, the nitrile-terminated compounds having Schiff bonds in the molecule are heated at a temperature below the temperature causing an exothermic reaction of said compounds, for example at 120°–180° C., to cause an addition reaction between two nitrile groups and one Schiff bond, producing a cross-ladder polymer having a dihydrotriazine ring in its structural unit. Thus, there is provided according to this invention a polymer having excellent heat resistance and generating no by-product gas at the time of molding since the reaction is not a condensation type.

What is claimed is:

1. A polymer obtained by polymerizing a nitrile-terminated Schiff compound monomer by heating said monomer to a temperature sufficient to cause polymerization but below the temperature at which an exothermic reaction occurs, said monomer represented by the formula:

$$X-(Z-Y-C\equiv N)_n$$

wherein n is a number of 1 or 2;

Z represents $-CH=N-$ or $-N=CH-$;

when n is 1, X represents a member of the group consisting of a $C_1$–$C_8$ alkyl group, a substituted or unsubstituted phenyl group, a substituted or unsubstituted naphthyl group, or a $C_3$–$C_6$ cycloalkyl group;

Y represents a member of the group consisting of a straight or branched alkylene group having 2 to 12 carbon atoms, a substituted or unsubstituted phenylene group, a substituted or unsubstituted naphthylene group, a substituted or unsubstituted biphenylene group, a substituted or unsubstituted anthracene group, a substituted or unsubstituted phenathrene group, a substituted or unsubstituted pyrene group, or a divalent organic group represented by the formula

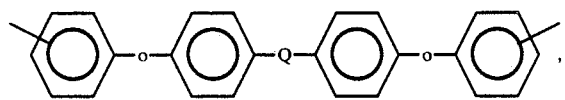

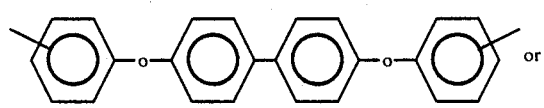

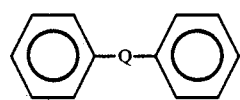

wherein Q represents O, S, $SO_2$, $-(CH_2)m-$, CO, $-(CF_2)_m-$,

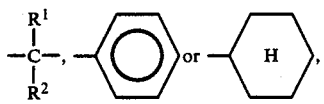

m represents a number of 1 to 12, and $R^1$ and $R^2$ are the same or different from one another and represent a member of the group consisting of H, $CH_3$, $C_2H_5$, $CF_3$,

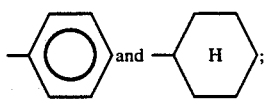

and when n is 2, X represents one of the divalent organic groups specified above wherein X and Y are the same or different from one another and a first Y the same or different from a second Y.

2. The polymer of claim 1 wherein said polymer has a cross-ladder skeleton structure.

3. The polymer of claim 1 further including a substituent selected from the group consisting of F, Cl, Br, $CH_3$, $CF_3$, OH, $NH_2$,

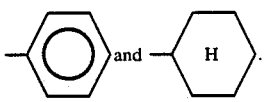

4. The polymer of claim 1 wherein n represents 2 and X represents a member of the group consisting of

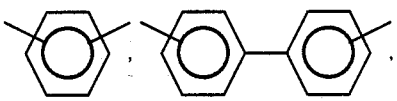

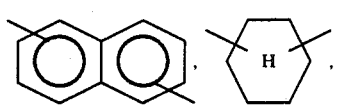

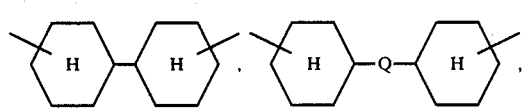

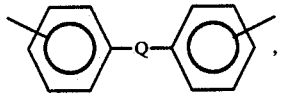

and —(CH₂)$_{m'}$—, wherein m' represents a number of 1 to 8, and Q represents a member of the group consisting of O, CO, S, SO₂ and

with R¹ and R² being the same or different from each other and representing a member of the group consisting of H, CH₃, C₂H₅, CF₃,

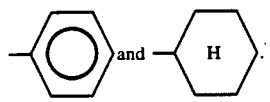

5. The polymer of claim 1 wherein n represents 1 and X represents a member selected from the group consisting of a C₁-C₈ alkyl group,

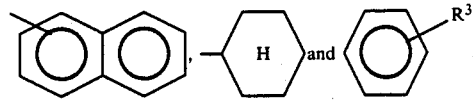

wherein R³ is a member of the group consisting of H, F, Cl, Br, CH₃, CF₃, OH, NH₂,

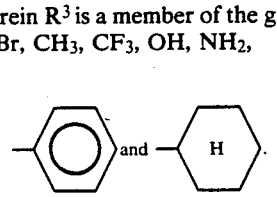

6. The polymer of claim 1 wherein said nitrile-terminated Schiff compound monomer is polymerized in the presence of an ethylenic polymerizable compound.

7. The polymer of claim 1 wherein said nitrile-terminated Schiff compound monomer is polymerized in the presence of an N, N'-substituted bismaleimide compound.

8. A polymer obtained by polymerizing a monomer of a nitrile-terminated Schiff compound represented by the formula

X—(Z—Y—C≡N)₂ wherein
Z represents —CH=N— or —N=CH—;
Y represents a straight or branched alkylene group having 1 to 12 carbon atoms, a substituted or unsubstituted phenylene group, a substituted or unsubstituted naphthylene group, a substituted or unsubstituted biphenylene group, a substituted or unsubstituted anthracene group, a substituted or unsubstituted phenanthrene group, a substituted or unsubstituted pyrene group or a divalent organic group represented by the formula

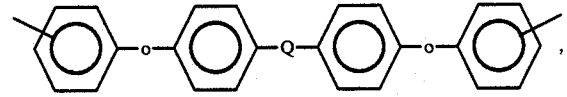

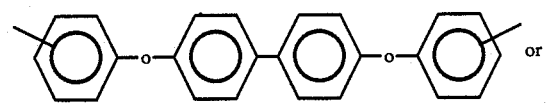

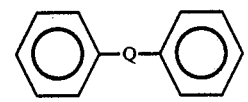

wherein
Q represents O, S, SO₂, —CH₂)$_m$ —, CO, —(CF₂)$_m$—,

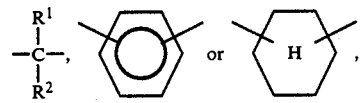

m represents a number of 1 to 12, and R¹ and R² are the same or different from one another and represent a member selected from the group consisting of H, CH₃, C₂H₅, CF₃,

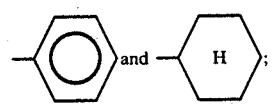

and

X represents one of the divalent organic groups specified above wherein X and Y are the same or different from one another and a first Y is the same or different from a second Y.

9. The polymer of claim 8 wherein said polymer has a cross-ladder skeleton structure.

10. The polymer of claim 8 wherein said polymer includes a substituent selected from the group consisting of F, Cl, Br, CH₃, CF₃, OH, NH₂,

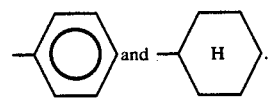

11. The polymer of claim 8 wherein X represents a member of the group consisting of

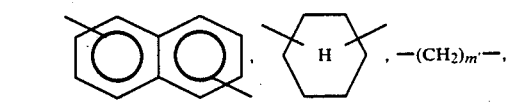

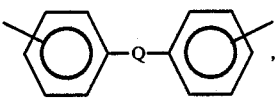

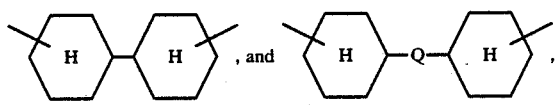

wherein m' represents a number of 1 to 8, and Q represents a member of the group consisting of O, CO, S, SO₂ and

with R¹ and R² being the same or different from each other and representing a member of the group consisting of H, CH₃, C₂H₅, CF₃,

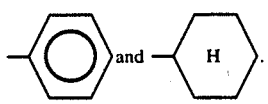

12. A process for producing a polymer, the process comprising:

providing a nitrile-terminated Schiff compound monomer represented by the formula

wherein

Z represents —CH=N— or —N=CH—;

Y represents a straight or branched alkylene group having 1 to 12 carbon atoms, a substituted or unsubstituted phenylene group, a substituted or unsubstituted naphthylene group, a substituted or unsubstituted biphenylene group, a substituted or unsubstituted anthracene group, a substituted phenanthrene group, a substituted or unsubstituted pyrene group or a divalent organic group consisting of

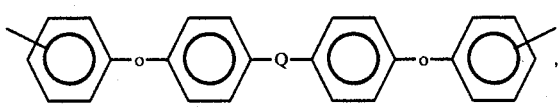

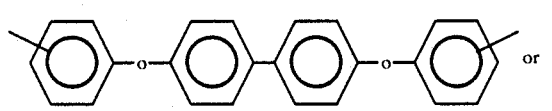

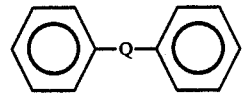

wherein Q represents O, S, SO₂, —(CH₂)ₘ—, CO, —CF₂)ₘ—,

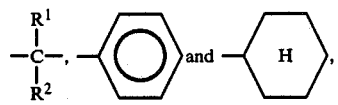

m represents a number of 1 to 12, and R¹ and R² are the same or different from one another and represent a member selected from the group consisting of H, CH₃, C₂H₅, CF₃,

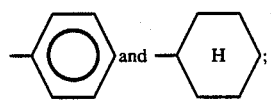

and

X represents one of the divalent organic groups specified above wherein X and Y are the same or different from one another and a first Y is the same or different from a second Y;

applying heat energy to the nitrile-terminated Schiff compound at a temperature sufficient to polymerize the same.

13. The process of claim 12 wherein the step of applying heat energy is replaced by a step of applying light energy.

14. The process of claim 12 wherein the step of applying heat energy to the nitrile-terminated Schiff compound calls for heating the monomer up to a temperature of about 180° C.

15. The process of claim 14 wherein the monomer is heated to a temperature between about 120° C. and 180° C.

16. The process of claim 12 wherein the polymer that is obtained includes a dihydrotriazine ring formed within its structural unit.

17. The process of claim 12 wherein the polymer that is obtained includes a cross-ladder skeleton.

18. The process of claim 12 further comprising the step of adding a cross-linking agent to the nitrile-terminated Schiff compound monomer.

19. The process of claim 18 wherein the cross-linking agent is an ethylenic polymerizable compound.

20. The process of claim 12 further comprising the step of adding an N, N'-substituted bismaleimide compound to the nitrile-terminated Schiff compound monomer.

21. A process for producing a polymer, the process comprising:

providing a nitrile terminated Schiff compound monomer represented by the formula

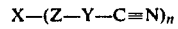

wherein n is a number of 1 or 2;

Z represents a —CH=N— or —N=CH—;

when n is 1, X represents a member of the group consisting of a $C_1$–$C_8$ alkyl group, a substituted or unsubstituted phenyl group, a substituted or unsubstituted naphthyl group, or a $C_3$–$C_6$ cycloalkyl group; and Y represents a member of the group consisting of a straight or branched alkylene group having 2 to 12 carbon atoms, a substituted or unsubstituted phenylene group, a substituted or unsubstituted naphthylene group, a substituted or unsubstituted biphenylene group, a substituted or unsubstituted anthracene group, a substituted or unsubstituted phenathrene group, a substituted or unsubstituted pyrene group, or a divalent organic group represented by the formula

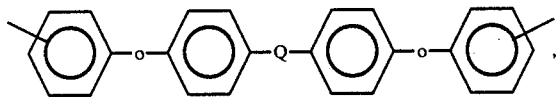

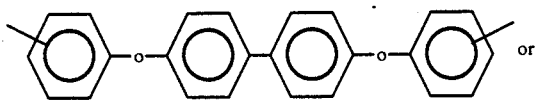 or

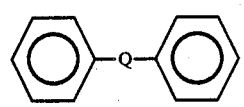

wherein Q represents O, S, $SO_2$, —$(CH_2)_m$—, CO, —$(CF_2)_m$—,

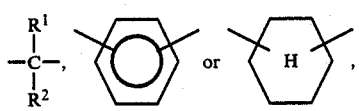

m represents a number of 1 to 12, and $R^1$ and $R^2$ are the same or different from one another and represent a member of the group consisting of H, $CH_3$, $C_2H_5$, $CF_3$,

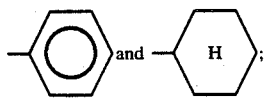

and when n is 2, X represents one of the divalent organic groups specified above wherein X and Y are the same or different from one another and a first Y is the same or different from a second Y;

giving heat energy to the monomer at a temperature between about 120° C. and 180° C. to polymerize the monomer.

22. The process of claim 21 further including the step of adding a cross-linking agent to the Schiff compound monomer compound.

* * * * *